United States Patent [19]

Simon

[11] Patent Number: 6,132,958
[45] Date of Patent: *Oct. 17, 2000

[54] FLUORESCENT BEAD FOR DETERMINING THE TEMPERATURE OF A CELL AND METHODS OF USE THEREOF

[75] Inventor: Sanford M. Simon, New York, N.Y.

[73] Assignee: The Rockefeller University, New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/320,874

[22] Filed: May 27, 1999

[51] Int. Cl.$^7$ ...................................................... C12Q 1/00
[52] U.S. Cl. ............................ 435/4; 435/968; 549/283; 526/347.2
[58] Field of Search ........................ 435/4, 968; 549/283; 526/347.2

[56] References Cited

U.S. PATENT DOCUMENTS

| | | | |
|---|---|---|---|
| 3,575,873 | 4/1971 | Carver et al. | 435/4 |
| 4,437,772 | 3/1984 | Samulski | 435/4 |
| 4,560,286 | 12/1985 | Wickershein | 435/4 |
| 4,735,907 | 4/1988 | Schaffer et al. | 435/4 |
| 4,819,658 | 4/1989 | Kolodner | 435/4 |
| 5,094,819 | 3/1992 | Yager et al. | 435/4 |
| 5,244,813 | 9/1993 | Walt et al. | 435/4 |
| 5,499,313 | 3/1996 | Kleinerman | 435/4 |
| 5,605,809 | 2/1997 | Komoriya et al. | 435/4 |
| 5,747,000 | 5/1998 | Platzek et al. | 435/4 |
| 5,928,625 | 7/1999 | Dorshow et al. | 435/4 |

OTHER PUBLICATIONS

Kolodner et al; Appl. Phys. Lett.; V.40, p782–784, 1982.
Chapman et al., 1995, Photochemistry and Photobiology, 62:416–425.
Kolodner et al, Appl Phys Lett, 40:782–4, 5–1982.
Kolodner et al, Appl Phys Lett; 42:749–51, 1–1983.
Kolodner et al, Appl Phys Lett, 42;117–9, 4, 1983.
Liu et al, J Thermophys Heat Trans, 9:605–11, 10–1995.
Liu et al, Exp. Therm Flu Sci, 10:101–112.
Liu et al, 1995, 30$^{th}$AIAA Thermophysics Conference/Jun. 19–22, San Diego, 1–7.
Olive, Int. J. Radiation Oncology Biol. Phys. 16:1565–1570, 6–1989.

Primary Examiner—Louise N. Leary
Attorney, Agent, or Firm—Klauber & Jackson

[57] ABSTRACT

The invention discloses a fluorescent bead that can be used for determining the temperature and/or metabolic state of a single cell contained in a cell/tissue sample. The fluorescent bead contains at least one temperature-sensitive fluorophore. The invention also includes methods of monitoring cellular metabolism and methods of diagnosing abnormal metabolism of a cell.

13 Claims, 4 Drawing Sheets

Bright-field image of cells     Thermal image of cells
FIG. 2A 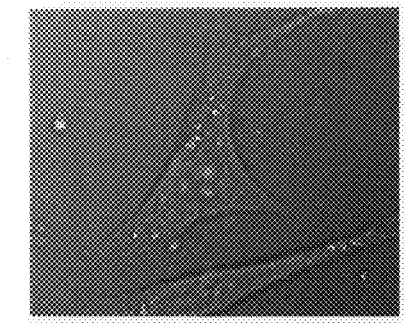 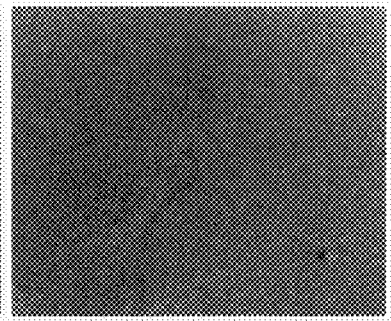 FIG. 2B
FIG. 2C 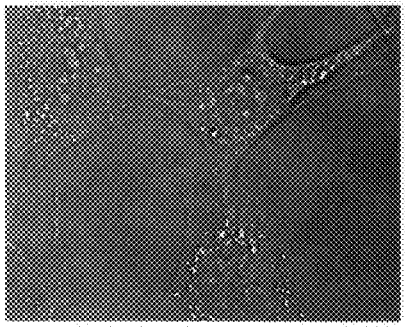 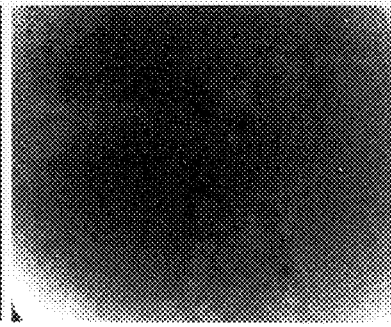 FIG. 2D

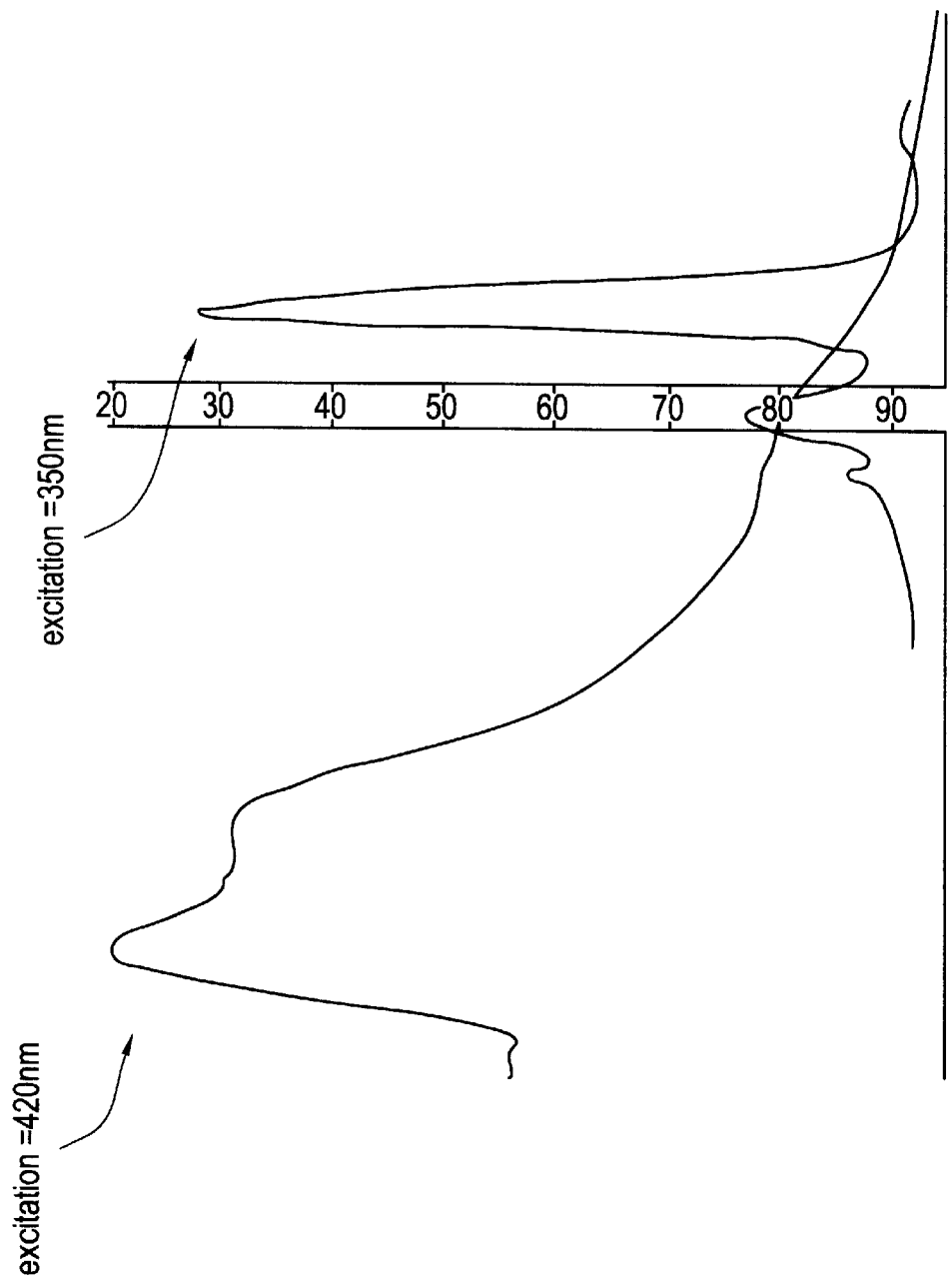

FLUORESCENT BEAD FOR DETERMINING THE TEMPERATURE OF A CELL AND METHODS OF USE THEREOF

FIELD OF THE INVENTION

The invention relates generally to novel methods of determining the temperature of a single cell, or group of cells, in a tissue sample. Methods of employing this method as a diagnostic aid are also included.

BACKGROUND OF THE INVENTION

Living cells require a stable rate of metabolism. Therefore in both cells and in the organisms containing the cells such regulation is under stringent control Approximately 50% of all energy in carbohydrates is converted into ATP and the rest is released as heat [Alberts et al., *Molecular Biology of the Cell*, (1989)]. The ATP, in turn, is used during growth for biosynthesis, or otherwise is used for work and the energy is released as heat. The release of this heat is used to warm the body in the form of temperature. Failure to maintain a stable metabolic level on an organismal level is a pathology referred to as fever, i.e., an increase in the temperature of an organism. Variations in metabolic levels are seen in a variety of pathological states including during bacterial or viral infections, in cancer, and in the general wasting away found during sepsis or cachexia.

The temperature of an organism is often taken as being indicative of the health of that organism. Even slight deviations in temperature may indicate a pathology. However the temperature of an individual cell cannot be assayed due to the limitation of current technology. Thus, it is not yet known to what extent cellular temperature varies with time within a cell or between two different cells. However, based on studies of large populations of cells there are good grounds to believe that some pathological states may be detectable by measuring temperature at the level of single cells.

Cellular metabolism may be regarded as the balance sheet for all of the enzymatic reactions occurring in the cell. Within this context, the net exothermic activity is seen as black body radiation, i.e., the heat that we assay when we measure the temperature of the cell. Prior studies of biological metabolic activity have used calorimetry which is applied at the level of an entire organism, or at the very least, an individual organ. Microcalorimetry can be applied to as few as 10 cells. However, there are severe limitations in the current technology limit resolving the heat production from single cells [Kemp, *Thermal and Energetic Studies of Cellular Biological Systems*, A. M. James, ed. (Bristol: Wright), pp. 147–166 (1987)]. The most sensitive technique applied to measuring metabolism in tumor cells is the Cartesian diver which can resolve hundreds of cells [Lutton and Kopac, Cancer Res., 31:1564–1569 (1971)]. This technique, however, is still too crude to resolve a heterogeneous population of cells, and it requires dissociation of the cells. Much of normal cell physiology is a dynamic process that requires cellular interaction in a three dimensional matrix. Many cellular activities are modified by cell-to-cell contact. All of this is lost when cells are dissociated. Recently, techniques have been developed to measure metabolites such as ATP, glucose and lactate in living cells [Hossman et al., *Acta Neuropathologica*, 69:139–147 (1986); Okada et al., *Journal of Neurosurgery*, 77:917–926 (1992)]. These techniques utilize photographic film [Hossman et al., 1986, supra; Okada et al., 1992, supra] or photon-counting cameras [Tamulevicius and Streffer, *British Journal of Cancer*, 72:1102–1112 (1995)] and have demonstrated considerable heterogeneity in metabolism in tumors when assayed with a millimeter spatial resolution.

Unfortunately, presently a number of important issues cannot be addressed because the metabolism of an individual cell cannot be determined. For example, we cannot presently study heterogenous populations of cells and resolve the activity of individual cells rather than the average of the mix. For example, a tumor is made of cancerous cells, normal cells, and infiltrating immune cells each of which is metabolizing at very different rates. In this case the measurement of the average metabolism of the tumor may not reflect the actual metabolism of the individual cells.

In most cells aerobic respiration is responsible for almost all of the production of ATP, with anaerobic glycolysis accounting for the remainder. It was noted over fifty years ago that anaerobic respiration is substantially increased in Ascites tumor cells relative to non-tumor cells [Warburg et al., *The Metabolism of Tumors*, ed. O. Warburg, Constable & Company LTD., London, pp. 129–170 (1930a); Warburg et al., *The Metabolism of Tumors*, ed. O. Warburg, Constable & Company LTD., London, pp. 254–265 (1930b)]. This led to the hypothesis that aerobic respiration was damaged in tumor cells [Warburg, *Science*, 123:309–314 (1956)]. As more has been learned about metabolism in the intervening years it was found that aerobic respiration is normal in tumor cells, but anaerobic respiration is increased. The mechanism responsible for this increase in anaerobic respiration is not presently understood. One major limiting factor in learning the mechanism is the inability to assay the relative metabolic levels of individual cells. As mentioned above, one particular problem is that tumors consist of a mix of normal, malignant, and immune cells. Current technology only allows the measurement of the average metabolism of this mixed population of cells. A second problem is the considerable heterogeneity even within the tumor cells. For example in tumors, oxygenation is often rate limiting for tumor growth [Kallinowski et al., *J. Cel. Physiol.*, 138:183–191 (1989)]. Thus, in rapidly growing tumors growth is limited by angiogenesis, the growth of new blood vessels for the delivery of oxygen and nutrients.

Chemotherapy is a powerful tool that is used to fight tumors. However, tumor cells frequently develop resistance to the chemotherapeutics. This resistance is observed as a decreased sensitivity to a broad spectrum of chemotherapeutic agents and such cells have been labeled multi-drug resistant [Simon et al., *Proc. Natl. Acad. Sci. USA*, 91:3497–3504 (1994); Schindler et al., *Biochemistry* 35, 2811–2817 (1996); U.S. patent application No. 09/080,739, filed May 18, 1998; and U.S. Pat. No. 5,851,789, Issued Dec. 22, 1998, the contents of which are hereby incorporated by reference in their entireties]. Although these cells were originally viewed as "super cells" capable of withstanding any therapeutic challenge, there is now growing evidence that multi-drug resistant cells escape chemotherapy by behaving more like normal cells; and in some ways these cells appear to have undergone a "reverse" transformation in their properties [Biedler et al., *Cancer & Metastasis Reviews*, 13:191–207 (1994)]. Once chemotherapeutic drugs are removed, these cells resume their aggressive malignant properties. It is not known what happens to the metabolism of multi-drug resistant cells during this period. Indirect results indicate that the level of anaerobic respiration in these cells have returned to the levels seen in non-transformed cells [Miccadei et al., *Oncology Research*, 8:27–35 (1996)]. Therefore there is a need to measure the metabolism of individual cells that are multi-drug resistant in order to diagnose when tumors are shifting from their quiescent multi-drug resistant phase into a more malignant stage. Furthermore, there is a need to provide a method of measuring the temperature of individual cells to determine the metabolic changes that occur in either normal or tumor cells. In addition, there is a need of a methodology for measuring the temperature of a cell from a fresh biopsy of living tissue in order to rapidly diagnose the tissue for the presence of tumor cells.

The emission of almost all fluorophores is affected by temperature, however, the use of fluorophores that are particularly sensitive to temperature was first used as a technique for calibrating temperature by Kolodner et al., [*Appl. Phys. Lett.* 40:782–784 (1982); *Appl. Phys. Lett.* 42: 782–784, (1983)]. Kolodner used a fluorophore, Eu(TTA)$_3$ embedded in a polymer, PMMA, to achieve temperature resolutions of 0.07° K. and of 10 $\mu$M spatial resolution. This temperature-sensitive fluorophore thus could be used to quantify temperatures.

A variety of fluorophores, including Eu(TTA)$_3$ have been solubilized into various solvents and polymers and used to "paint" airplane wings in the laboratory of John P. Sullivan (Pursue University, see Table 1 modified from [Campbell et al., *Temperature Sensitive Fluorescent Paint Systems,* 18:94–2483 (1994)]). The change in fluorescence can be used to monitor the temperature changes of the airplane wing in a wind tunnel, for example. To date, temperature-sensitive fluorophores have been used in integrated circuit diagnostics [Kolodner et al., *Appl. Phys. Lett.,* 42:117–119 (1983)], to detect boundary layer transition on a two-dimensional wing, and to visualize the interaction between the leading edge vortices and the surface of a delta wing [Campbell et al., in sixth Intern. Symp. on Applications of Laser Techniques to Fluid Mechanics, Lisbon, Portugal (1992); Campbell et al., *Temperature Measurement Using Fluorescent Molecules,* Abstract ( 1992); Campbell et al., *Temperature Sensitive Fluorescent Paint Systems,* 18:94 2483 (1994); Hamner et al., *A Scanning Laser System for Temperature and Pressure Sensitive Paint,* 32:94–0728 (1994)].

The citation of any reference herein should not be construed as an admission that such reference is available as "Prior Art" to the instant application.

SUMMARY OF THE INVENTION

The present invention, provides a means of measuring the temperature of a cell by using a temperature-sensitive fluorophore and a temperature insensitive fluorophore which have been encased in a bead. One aspect of the present invention provides a fluorescent bead that comprises at least one temperature-sensitive fluorophore and at least one temperature-insensitive fluorophore embedded in a polymeric material. In a particular embodiment, such a polymeric fluorescent bead comprises one temperature-sensitive fluorophore and one temperature-insensitive fluorophore embedded in the polymeric material.

Preferably, the fluorescence emission due to a temperature-sensitive fluorophore and that due to a temperature-insensitive fluorophore can be resolved from each other. In a particular embodiment of the polymeric fluorescent bead, the temperature-sensitive fluorophore is Eu(TTA)$_3$ [see, U.S. patent application No. 09/003,628, filed Jan. 7, 1998, the contents of which is hereby incorporated herein by reference in its entirety]. In another embodiment of the polymeric fluorescent bead, the temperature-insensitive fluorophore is coumarin. In a preferred embodiment the temperature-sensitive fluorophore is Eu(TTA)$_3$, and the temperature-insensitive fluorophore is coumarin. In one embodiment the fluorescent bead is 40–150 nm in size. In a preferred embodiment the fluorescent bead is 60–110 nm in size. In a more preferred embodiment of this type, the polymeric fluorescent bead is 80–90 nm in size.

In a particular embodiment the polymeric fluorescent bead is made of polystyrene. In another such embodiment the polymeric fluorescent bead is made of a non-aromatic synthetic polymer. In one such embodiment the polymeric fluorescent bead is made of poly(methyl methacrylate) (PMMA). The present invention also provides methods of making the polymeric fluorescent beads of the present invention.

In addition, the present invention provides methods of using the polymeric fluorescent beads of the present invention. For example, the present invention provides methods of determining the temperature of a cell. One such method comprises placing the polymeric fluorescent beads of the present invention into a cell. The temperature-sensitive and temperature-insensitive fluorophores are then excited with the appropriate ultraviolet, visible, or infrared light and the fluorescent signal emitted by the temperature-sensitive and temperature-insensitive fluorophores are detected. When the temperature-sensitive fluorophore and the temperature-insensitive fluorophore are excited with the appropriate ultraviolet, visible or infrared light they emit detectable fluorescent signals which can be individually resolved. Preferably the fluorescent signal due to the temperature-sensitive fluorophore is affected by the metabolic rate/temperature of the cell while that of the temperature-insensitive fluorophore is not. However, the critical issue is that for a given bead construct, the fluorescence change of the temperature-sensitive fluorophore of the bead due to temperature changes in a cell is sufficiently different than that of its temperature-insensitive fluorophore partner. This allows the distinction between temperature changes in the cell and fluorescence changes due to movement of the beads (e.g., local bead concentration changes) in the cell. Thus, the intensity of the fluorescent signal detected for temperature-sensitive fluorophore is indicative of the temperature of the cell, when corrected for the local bead concentration, by the corresponding emission of the temperature-insensitive fluorophore.

In a related embodiment, in place of a bead comprising a temperature-sensitive fluorophore and a temperature-insensitive fluorophore, the present invention provides a bead that comprises two temperature-sensitive fluorophores that have opposite temperature dependencies. Thus, one fluorophore has an increased fluorescence emission at a higher temperature, whereas the other has a decreased fluorescence emission at a higher temperature. Over the relevant temperature range, as discussed herein, these temperature-sensitive fluorescence changes would preferably be linear and/or pre-calibrated. In any case, a change in cellular temperature would shift the ratio of fluorescence of the two fluorophores allowing the temperature change to be determined of a cell that contains the beads. On the other hand, whereas the movement of the beads in the cell could result in an absolute change in the fluorescence emission measured, the ratio of the fluorescence emission due to the two fluorophores would remain unchanged.

The present invention further provides methods of detecting the metabolic activity of a cell using the polymeric fluorescent beads of the present invention. One such embodiment comprises determining the temperature of the cell with the polymeric fluorescent beads of the present invention as described above, and correlating the temperature with its metabolic activity.

The present invention also provides methods of detecting the presence of abnormal metabolism of a cell surrounded by healthy tissue in a tissue sample using the polymeric fluorescent beads of the present invention. One such embodiment comprises determining the temperature of the cell. A difference in temperature of the cell relative to a control cell, is indicative that the cell is undergoing abnormal metabolism In a particular embodiment of this type the tissue sample is obtained from a tumor biopsy. In another embodiment the abnormal metabolism of the cell is indicative of ultraviolet damage. In still another embodiment the abnormal metabolism of the cell is indicative cachexia. In yet another embodiment the abnormal metabolism of the cell is indicative apoptosis.

When the fluorophores are excited with the appropriate ultraviolet, visible, or infrared light, the fluorophores emit detectable fluorescent signals. When the fluorescent bead is placed into a cell, the intensity of the fluorescent signal of the temperature-sensitive fluorophore is affected by the metabolic rate of the cell, whereas the fluorescent signal of the temperature-insensitive fluorophore is substantially less, (or preferably completely) unaffected by the metabolic rate of the cell.

Preferably the fluorescent bead contains fluorophores that can emit stable fluorescent signals while the bead is adjacent to an aqueous solution for at least one hour upon excitation with light (e.g., ultraviolet, visible, or infrared) at 37° C., at about pH 7.5. In a particular embodiment, when the fluorescent bead is placed in a living cell, the fluorescent-sensitive fluorophore shows a 1% to 2.5% change in intensity of its fluorescent signal relative to the corresponding change in the fluorescent signal of the temperature-insensitive fluorophore, per degree Celsius increase in temperature.

In a particular embodiment of the present invention, a cell containing a fluorescent bead is placed on a microscope, the fluorophores are excited, and their emission are detected using the microscope. In one such embodiment, the microscope is a laser scanning confocal microscope that is equipped with an ultraviolet laser for excitation. In another such embodiment the microscope is a fluorescent microscope equipped with a Hg or Xenon lamp with a ultraviolet excitation filter, and a visible emission filter of 615 nm +/−10 nm.

These and other aspects of the present invention will be better appreciated by reference to the following drawings and Detailed Description.

BRIEF DESCRIPTION OF THE DRAWINGS

FIGS. 2A and 2C are cells as described in the Example viewed by absorbance spectroscopy.

FIGS. 2B and 2D represent the fluorescence difference spectra obtained from the cells of FIGS. 2A and 2C respectively, after the addition of FCCP. The cells were excited at 355 nm and the emission was monitored at 614 nm.

FIG. 3 shows the emission spectra of beads containing $Eu(TTA)_3$ and coumarin. When the excitation was performed at 350 nm, only a peak at 614 nm was observed, indicative of the fluorescence of europium in the $Eu(TTA)_3$. When the excitation was performed at 420 nm, there was a large peak at 480 nm due to coumarin, whereas only a minimal emission at 614 nm was observed.

FIG. 4(lower plot) shows the corresponding ratio of fluorescence intensity of $Eu(TTA)_3$:coumarin with temperature. The fluorescent beads were excited at 420 nm and monitored at 480 nm for coumarin. The two sets of symbols for each experiment are from two different runs on the same sample.

DETAILED DESCRIPTION OF THE INVENTION

Figure 1:
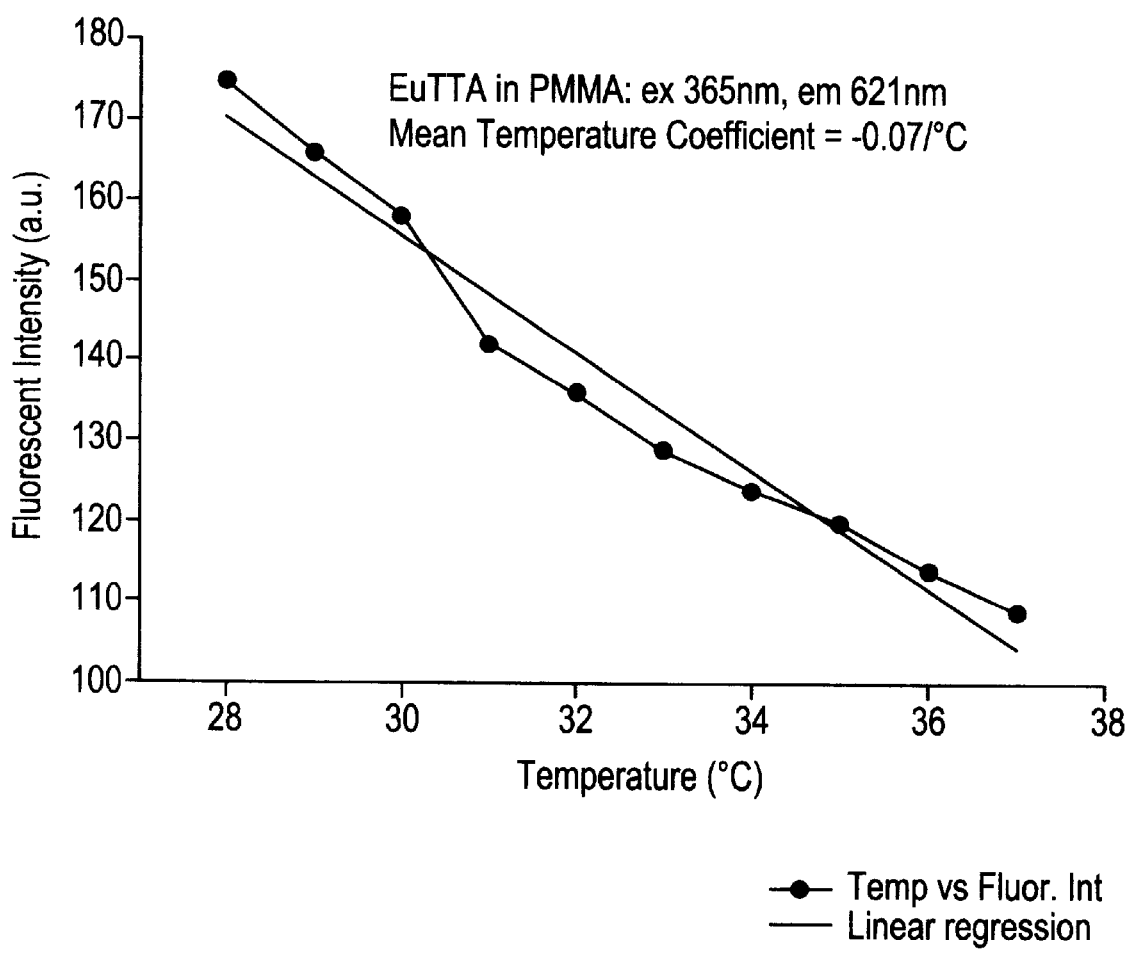
FIG. 1 depicts the change in fluorescence intensity with temperature for $Eu(TTA)_3$/PMMA. The excitation wavelength was 365 nm and the emission wavelength was 621 nm.

The present invention provides methods for using fluorescent beads, as described herein, to monitor the temperature and/or metabolic changes of a single cell or group of cells. The cell can either be dissociated from other cells, or alternatively remain part of a cell sample. For example, when the cell is a tumor cell, such monitoring allows new insights into the metabolic changes of tumor cells. This, in turn, aids in the understanding of the general cell biology of tumor cells.

In addition, the fluorescent beads of the present invention may be used to determine whether tumor cells are present in a fresh biopsy of living tissue in a time frame which would allow the diagnosis to occur during the tumor biopsy. In this manner, the analysis of the biopsy could be made immediately following the removal of the tissue, allowing a health practitioner to immediately make a decision on whether additional tissue must be removed, or alternatively, conclude that no further surgery is required. Such a procedure has many advantages over current technology which requires an initial biopsy, then typically a 7 to 10 day assessment of the tissue, which many times is followed by an additional surgical procedure. Thus, the present invention allows the medical practitioner to perform one surgical procedure and to immediately react to the tissue analysis thereby preventing further deterioration of the tissue during the time span of the analysis.

The present invention also includes methods of determining the temperature of a cell using the fluorescent beads of the present invention. In a preferred embodiment, the fluorescent beads of the present invention comprise at least one temperature-sensitive fluorophore and at least one temperature-insensitive fluorophore which are both embedded into a bead which is preferably a polymer, e.g., polystyrene or PMMA.

The beads can be made from any of a number of solid support materials as long as the material is essentially impermeable to water (e.g., such as polystyrene or PMMA). The beads can be prepared by standard technology, and/or obtained from any of a number of commercial sources. Pre-made solid support beads can then be swollen in the presence of the fluorophores, thereby trapping the fluorophores in the beads. It is preferable not to use solid support beads that are permeable to water since the fluorescence due to the embedded fluorophores should be independent of changes in the solution, e.g., salt concentrations, pH, etc.

The fluorescent beads can then be loaded into a cell. The fluorescent beads can be placed into the cells by Scrape loading the cells, as exemplified below, [McNeil et al., *J.*

Cell Biol. 98:556–1564 (1984); Altan et al., *Journal of Experimental Medicine* 187:155–175. (1998)] or by microinjection of beads [Tanasugarn et al., *J. Cell Biol.* 2:717–724 (1984)]. In an alternative embodiment the fluorescent beads are loaded into the cell by syringe loading. The cells are dissociated from their substrate with trypsin and EDTA and then passed back and forth between two syringes in the presence of the beads [Clarke and McNeil, *J. Cell Sci.*, Pt3:533–541 (1992)]. Still another method entails allowing the cells to endocytose the beads in a hyperosmotic media and then shock the cells in a hypo-osmotic media that causes the endosomes to lyse open inside of the cells [Okada and Rechsteiner, *Cell* 29:33–41 (1982)].

The bead shields the fluorophores from the cytosol of the cell protecting the fluorophores from being affected by changes of ions or viscosity. This is an important aspect of the invention since most fluorophores are affected by their environment, i.e., changes in the solvent, the salt concentration, the temperature, or the viscosity of the media can all affect the fluorescence properties of a fluorophore. In a preferred embodiment of the invention, only heat penetrates into or leaves the fluorescent beads, thereby allowing the temperature of the cytosol, or cytosolic compartment to be determined most accurately.

In one aspect of the present invention the fluorescent beads contain at least one temperature-sensitive fluorophore, and at least one temperature-insensitive fluorophore in order to allow for the unavoidable changes in the distribution of the beads in a cell which could, in turn, lead to a corresponding change in the local concentration of fluorophore. Thus by co-embedding a fluorophore that has minimal sensitivity to temperature with a temperature-sensitive fluorophore, the temperature-insensitive fluorophore serves as a control for changes in fluorescence due to the distribution of the beads in the cell. This allows an accurate calibration of the fluorescence of the fluorescent beads as a function of temperature.

Therefore, if appearing herein, the following terms shall have the definitions set out below:

As used herein, a "metabolic probe" comprises a solid substrate containing a temperature-sensitive fluorophore embedded in a polymer, wherein, when the fluorophore is excited with the appropriate wavelength of light (e.g. ultraviolet, visible or infrared) the fluorophore emits a detectable fluorescent signal, and wherein, when a living cell (alone, or as part of a cell sample) is placed on the metabolic probe, or the metabolic probe is placed into a cell, the fluorescent signal is potentiated (i.e., increases or decreases) due to the heat emitted by the cell (e.g., as measured as the temperature and/or metabolic state of the cell). The fluorescent beads of the present invention are a particular type of a metabolic probe.

As used herein, a "solid substrate" can be made of any solid material, preferably a plastic, metal, or glass. The solid substrate used for the fluorescent beads of the present invention are preferably impermeable to aqueous solutions.

As used herein "about pH 7.5" includes the pH range of pH 7.0 to pH 8.0.

As used herein, a temperature-sensitive fluorophore is a compound whose emission intensity varies monotonically as a function of temperature over at least the region of 35–40° C. In one embodiment the fluorophore has an exponential or linear dependence upon temperature of between 0.25–2.5% change in fluorescence emission intensity per degree centigrade. A preferred fluorophore has an exponential or linear dependence upon temperature of at least a 1% change in fluorescence emission intensity per degree centigrade.

As used herein, a "temperature-insensitive fluorophore" is a fluorophore that is substantially unaffected by the metabolic rate of the cell, e.g., a fluorophore whose emission intensity varies by less than 0.1% per degree centigrade, and preferably less than 0.025% per degree centigrade.

As used herein, a "fluorescent bead" comprises at least two different fluorophores embedded into the bead that due to the distinct fluorescent properties of the fluorophores, the bead can be used to measure temperature changes in a cell. In one embodiment the fluorescent bead comprises at least one temperature-sensitive fluorophore and at least one temperature-insensitive fluorophore. The fluorophores are embedded into a bead (which is preferably a polymer) wherein, when either or both fluorophores are excited with the appropriate wavelength of light (e.g. ultraviolet, visible or infrared) the fluorophore(s) emit detectable fluorescent signals, and wherein, when the bead is placed into a living cell (a lone cell, or a cell sample) the fluorescent signal of the temperature-sensitive fluorophore is potentiated (i.e., increases or decreases) due to the heat emitted by the cell (e.g., as measured as the temperature and/or metabolic state of the cell) in a manner that is distinguishable from that of the temperature-insensitive fluorophore. In another embodiment, the bead comprises two temperature-sensitive fluorophores that have opposite temperature dependencies. Thus, one fluorophore has an increased emission at a higher temperature, whereas the other has a decreased emission at a higher temperature.

In one application of the present invention, the temperature is determined of a cell obtained from a cell sample from a patient suspected of suffering from cachexia. Cachexia is a disease state that wastes away the body, and often is fatal. Cachexia, which is triggered by tumor necrosis factor, is associated with increased production of lactic acid and is believed to be the result of activating a futile substrate cycle between fructose 6-phosphate and fructose 1,6-bisphosphate. This depletes cellular ATP [Zentella et al., *Cytokine*, 5:436–447 (1993)]. Thus, a determination of an increased temperature for cells obtained from a patient suspected of having cachexia is consistent with the diagnosis of cachexia.

In another aspect of the present invention, the mechanism of induced fever by macrophage inflammatory protein can be probed. Fever can be elicited in animals by a factor that is released by macrophages: macrophage inflammatory protein [Myers et al., *Neurochemical Research*, 18:667–673 (1993)]. While it is known that this factor modulates food intake by the animal, it is not yet known where or how it causes cells to increase metabolism and increase temperature. Thus, determining which particular cells (or cell types) are emitting the excess heat (and thereby causing the fever) can be accomplished by determining the temperature of the individual cells (or cell type).

In a particular aspect of the present invention, the temperature of cultured cells are determined. In one such embodiment, populations of breast tumor cells are used. In another such embodiment, drug-resistant breast tumor cells are used. In yet another embodiment, non-transformed breast cells are used. In a preferred embodiment, two of these cell-types are used. In yet a more preferred embodiment, all three cell types are used. In a preferred embodiment, the breast tumor cells are from a human source. In one particular embodiment, brown adipose tissue cells from tumor cell line HIB 1B are used.

In another embodiment of this aspect of the invention, biopsies of human tissue are used as the cell source. In a particular embodiment, fresh biopsy of breast tissue is used as the cell source. A slice through the breast includes fat cells (which are filled with large fat globules that have very low metabolic levels) and duct cells which are actively metabolizing and secreting. The basal metabolic rate of tumor cells is significantly higher than that of "normal" cells. Assays using surface thermometry of skin tumors indicate a temperature difference (upon illumination) of up to 3.3° C. In another embodiment, the biopsy is of colon tissue.

In current medical practice, excised tissue obtained during biopsies is prepared for histological assays taking 7–10 days. Thus, the patient is no longer in the surgery room when the results are determined. Subsequent surgery therefore, often needs to be scheduled. The method of determining the temperature of cells in the slices using the methodology of the present invention, allows the cells of the tissue slices to be immediately assayed using a standard fluorescence micro scope to determine if there are localized "hot spots" of metabolic activity (i.e. cells emitting greater that normal quantities of heat) as a fingerprint for tumor cells. Such determinations allow the surgeon to immediately decide whether or not to excise additional tissue.

Still another aspect of the invention includes determining the temperature/metabolism of individual cells, to monitor the shift of quiescent multi-drug resistant cells to the more malignant state. In this case an increase in temperature would be consistent with such a shift. Such monitoring might be particularly useful during chemotherapy, and more particularly, after the end of such treatment.

In a particular embodiment, the fluorescent beads of the present invention are placed in a cell or tissue biopsy and then detected with a laser scanning confocal microscope that is equipped with a laser for excitation which allows essentially simultaneous emission measurements from the temperature-sensitive fluorophore and temperature-insensitive fluorophore. In another such embodiment the detection is performed on a fluorescence microscope equipped with a Hg or Xenon lamp with appropriate excitation filters and emission filters for monitoring the fluorescence emission of the fluorophores. If a bead is used with a temperature-sensitive fluorophore and a temperature-insensitive fluorophore the temperature can be calibrated from the ratio of the emission of the temperature-sensitive fluorophore to the emission of the temperature-insensitive fluorophore. On the other hand, if the bead is used with two temperature-sensitive fluorophores having opposite temperature dependence (see above) the temperature can be calibrated from the ratio of the emission of the two fluorophores.

As mentioned above, a preferred temperature-sensitive fluorophore for the fluorescent bead is $Eu(TTA)_3$ which has an excitation maximum of 355 to 360 nm and has an emission maximum of 614 nm. In a particular embodiment of the fluorescent bead, $Eu(TTA)_3$ is combined with a temperature-insensitive fluorophore and a polymer, e.g., poly(methyl methacrylate), (PMMA). However, other suitable combinations are envisioned by the present invention. Such potential combinations are exemplified in Table 1. These and other combinations can be tested to determine their suitability to serve as a components of the fluorescent beads.

In a particular embodiment of the fluorescent bead, $Eu(TTA)_3$ and coumarin are embedded in polystyrene. In a related embodiment of the fluorescent bead, $Eu(TTA)_3$ and coumarin are embedded PMMA. Other materials and combinations thereof can be readily tested, including by the methodology described herein, to determine their suitability to serve as a components of the fluorescent bead.

The present invention therefore provides a fluorescent bead that can be used to determine the metabolic rate of a cell. The value of the temperature-sensitive fluorophore is to detect the metabolic rate, whereas the value of the temperature-insensitive fluorophore is to allow the calibration of the concentration of fluorescent beads, e.g. to distinguish a change in fluorescence due to the movement of the beads from a change in fluorescence due to a change in temperature. Therefore, appropriate pairing of temperature-sensitive and temperature-insensitive fluorophores can be formulated depending on the circumstances of the particular measurement being made.

The key criteria for choosing a temperature-sensitive fluorophore and temperature-insensitive fluorophore pair for a fluorescent bead of the present invention are (i) that the temperature-sensitive fluorophore show a maximal change of fluorescence with change in temperature at 37° C. preferably while embedded in a polymer whereas, (ii) the temperature-insensitive fluorophore show a minimal change of fluorescence with change in temperature at 37° C. preferably while embedded in a polymer; and both fluorophores (iii) have the ability to be embedded in a polymer and away from the aqueous solution; (iv) be non-toxic to living cells, (v) act as independent fluorophores (e.g., not undergo fluorescence energy transfer, have Forster energy interactions, or act as quenching agents for each other etc.) and (vi) have fluorescence spectra that allows them to be readily resolved from each other.

The fluorophores can be tested by determining their sensitivity to temperature changes at 37° C., their stability in an aqueous environment, their stability during embedding into the polymer, and their resistance to photobleaching (such resistance is required for long-term observations and subsequent calibrations). The greater the temperature-sensitive fluorophore's sensitivity to temperature change at 37° C., (and the corresponding lack of sensitivity to temperature change at 37° C. of the temperature-insensitive fluorophore), the greater their stability under the above-mentioned conditions, including resistance to the photobleaching, the more suitable are the fluorophores as components of the fluorescent beads. Similarly, the polymer is selected for having an optimizing effect on the fluorophores. Finally, the fluorophores/polymer combination must be compatible with the living cells, i.e., they should not adversely affect cell viability.

In a particular embodiment the polystyrene fluorescent bead is 80–90 nm size. In general, the size of the beads should be optimized for loading into the cells. The preferred range is between about 40 to 150 nm. Beads that are smaller than 40 nm have a tendency to aggregate (primarily from charge effects) but are otherwise acceptable; whereas, beads that are larger than 150 nm are somewhat more difficult to load into the cell and could also potentially disrupt cellular structure. Larger beads can be loaded into the cell through a number of techniques including by osmotic shock.

The surface of the fluorescent beads is preferably designed to minimize aggregation of the beads after injection into cells (e.g., the beads used in the Example below, were covered with carboxyl groups). Alternatively, the beads can be coated with a particular agent to target them to subcellular compartments. A hydrophobic coat would facilitate binding to cellular membranes. A peptide coat that targets proteins to the mitochondria will localize the beads to the mitochondria. Similarly, a targeting signal peptide could also be used for chloroplasts or the endoplasmic reticulum. In addition, the fluorescent beads can be coated with a specific antibody or antigen binding fragment thereof. Indeed, if the surface of the beads is not modified, the beads may either aggregate or bind to the cell matrix and therefore not move. Therefore, either positive or negative charges at various densities on the surface of the beads can be effective.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

Fluorescent Beads for Use as a Metabolic Probe

Introduction

In tissues, or between tissues, it is intuitive that there be variations in cellular activity as well as in metabolism. However, the correlation between the variations in metabolic activity varies and cellular activity has not been determined. It is also unknown whether there are gradients of metabolism on a cellular level, e.g., differences in metabolism between growth cones and cell bodies, or between dendrites and axons. Furthermore, it is unknown whether such potential gradients can be stimulated by growth factors or other hormonal factors. The present invention provides a means for determining at least some of the answers to these important metabolic questions through the use fluorescent beads that contain both a temperature-sensitive fluorophore and a temperature-insensitive fluorophore. The fluorescent beads can then be loaded into cells as temperature/metabolic probes.

Several criteria have been introduced in order to select appropriate fluorophores and polymers for the fluorescent beads of the present invention, including the determination of: (i) optimal excitation and emission spectrum by recording excitation and emission scans; (ii) photobleaching rate and stability in water (tested by recording the average fluorescent signal over time); and (iii) temperature coefficient (change of intensity per degree) which can be determined by recording fluorescent intensity changes during temperature changes of normally 1° C. For example, the sensitivity of the temperature-sensitive fluorophore to temperature changes at 37° C. is an important criteria, with greater sensitivity being desirable, whereas corresponding minimal changes are required for the temperature-insensitive fluorophore. Similarly, the fluorophores are selected for their stability in an aqueous environment, since a viable cell is most stable in an aqueous environment. In addition, a fluorophore is selected for its stability during its embedding into a polymer. For a bead that is 100 nm, a thin layer of polymer can still separate the fluorophore from the cellular secretion of a protein, metabolite, or ion, that could otherwise modify the properties of the fluorophore.

Further, a polymer is selected which optimizes the properties of the fluorophores, particularly properties that allow the two fluorophores to be distinguished, e.g., fluorescence emission and/or excitation spectra, and temperature sensitivity. Such a polymer should also be selected for relative resistance to photobleaching (a property required for long-term observations and subsequent calibrations). Furthermore, a polymer, and the fluorophore should be compatible with living cells so as to ensure that the polymer and fluorophore do not adversely affect cell viability.

Materials and Methods

Synthesis of Fluorescent Beads

Two different polymers, polystyrene and PMMA were used in the manufacture of fluorescent beads containing the temperature-sensitive fluorophore, $Eu(TTA)_3$ [Europium Thenoyl trifluoroacetonate, abbreviated $Eu(TTA)_3$ or EuTTA (Advanced Materials, New Hill, N.C.)], and the temperature-insensitive fluorophore, coumarin (Sigma Chemical Co., or Molecular Probes).

The beads made of polystyrene were 80–90 nm size. The polystyrene bead proved to be more stable, however, it also appeared to interfere with the fluorescence of the $Eu(TTA)_3$; in general the fluorescence intensity in polystyrene was 40% of the fluorescence intensity in PMMA. The surface of the beads were covered with carboxyl groups that appeared to minimize aggregation of the beads after injection into cells.

Placing the Fluorescent Beads into the Cells

The fluorescent beads are placed into the cells by Scrape loading the cells [McNeil et al., *J. Cell Biol.* 98:556–1564 (1984); Altan et al., *Journal of Experimental Medicine* 187:155–175. (1998)]. Briefly, the cells are plated on polystyrene plates at 50% confluency 24–36 hours prior to loading the beads. The medium is aspirated off the dishes, and the cells are covered with 50 $\mu$l of the beads. The cells are then quickly scraped off the polystyrene with a rubber scraper and placed in pre-chilled tubes containing 1 ml of media without serum. The cells are then harvested by spinning at 100 g for five minutes. The media is aspirated and replaced again with pre-chilled media without serum. The cells are then harvested again by spinning. Finally the media is aspirated and replaced with media containing serum. The cells are then plated on poly-lysine coated glass cover-slips.

Tissue Culture cells as a Model System

Populations of human breast tumor cells, drug-resistant human breast tumor cells and non-transformed breast cells as well as brown fat cells that produce heat in hibernating animals can be used as the cells for the initial in situ studies for optimizing the fluorescent bead temperature determinations, e.g., MCF-7/ADR cells are a cell line resistant to chemotherapeutics which is derived from a human breast carcinoma. They are maintained in Modified Eagle's medium with phenol red, L-glutamine, Bovine insulin 10 $\mu$g/ml, and 10% FBS in a humidified incubator at 37° C. and 5% $pCO_2$ (Forma Scientific, Ohio). In addition, the MCF-7/ADR cells are continuously maintained in 0.8 $\mu$M Adriamycin.

Fluorescent Measurements

Twelve to twenty-four hours prior to an experiment the cells are loaded with fluorescent beads. The cells are usually scrape loaded with the beads and allowed 24 hours to recover. To reduce background fluorescence the cells are plated in media without phenol red. The cells are then loaded in a chamber (e.g., a Bioptecs closed imaging chamber) on an inverted microscope.

Cells are observed in an Olympus fluorescence microscope equipped with a Xenon lamp, a Uniblitz shutter (Vincent and Associates, Rochester, N.Y.) and filter wheels both on the excitation and emission side. The shuttering of the light source is controlled with a computer. A filter holder was manufactured to hold various filters including a 355 nm excitation filter, a 450 nm excitation fitter and a 490 nm excitation filter. The data are collected on a Hamamatsu 4972 (ORCA) cooled charged coupled device (Hamamatsu Photonics) and digitized with software written in National Instruments Lab View. Cells are visualized in a temperature controlled chamber with a constant perfusion of media which is equilibrated with 5% $CO_2$ at 37° C. The objectives were kept heated at 37° C.

The cells are alternatively excited with a λex of 355 nm and λem of 614 (to record the $Eu(TTA)_3$ fluorescence, e.g., the temperature-sensitive fluorophore) and then excited at λex of 428 nm and λem of 480 (to record the coumarin fluorescence, e.g., the temperature-insensitive fluorophore). When the ratio was taken of successive images, the cells could not be detected. However, upon inclusion of FCCP, an proton-ionophore which increases the proton permeability of the mitochondria and thus increases the hydrolysis of ATP, there is an increased fluorescent emission consistent with an increase of temperature. The greatest increase of temperature is approximately 100° mK and it is most consistently observed in the growth cone of the cell (FIGS. 2B and 2D).

Results

The temperature-sensitive fluorophores studied change their fluorescence in response to temperature. However, their fluorescence could also be sensitive to particular proteins, carbohydrates, pH or ionic changes. Therefore, the fluorophore is embedded in a polymer that can be used to coat the beads. Polystyrene is one such support polymer. It is stable to many different treatments, it is non-toxic, and it can be used as a substrate for growing cells. The response properties of $Eu(TTA)_3$ to temperature are not optimal in the polystyrene. It appears as if the benzene rings in the polystyrene adversely interacted with the groups in the $Eu(TTA)_3$ resulting in a loss of fluorescence activity. On the other hand, PMMA, Poly(methyl methacrylate) is a non-aromatic fluorophore. This polymer had been known to be sensitive to the ultraviolet wavelengths used to excite EU-TTA. However, a mixture of $Eu(TTA)_3$ and PMMA can be immersed in a water environment without adverse effects on mechanical stability; and the fluorescent signal of the $Eu(TTA)_3$ is stable for at least an hour during UV excitation. Water does not adversely affect the fluorescent signal; and the fluorescence changes 2.5% for every one degree change centigrade. Furthermore, the noise is very low (approximately 100:1) allowing the resolution of changes of 0.01° C. A plot of the change in fluorescence intensity with temperature is depicted in FIG. 1. In Table 1, the $Eu(TTA)_3$/PMMA mixture is compared with a sampling of other fluorophore/polymer couples in regard to their maximum Log Slope/°C.

TABLE 1

| Fluorophore | Polymer | Maximum Log Slope/° C. | Temp |
|---|---|---|---|
| Anthracene | Cellulose Acetate | | |
| Coumarin | PMMA | −0.004 | 60 |
| CuOEP | GP-197 | −0.0113 | −100 |
| Erythrosin B | Polycarbonate | | |
| Europium thenoyltrifluoroacetonate $(Eu(TTA)_3)$ | model airplane dope | −0.036 | 0 |
| Europium thenoyltrifluoroacetonate $(Eu(TTA)_3)$ | PMMA | −0.049 | |
| Europium thenoyltrifluoroacetonate $(Eu(TTA)_3)$ | marathon | −0.0095 | |
| HC-295 | GP-197 | | |
| $La_2O_2S:Eu(1\%)$ | solid | −0.0031 | −150 |
| Perylene | model airplane dope | −0.0134 | 25 |
| Perylenedicarboximide | PMMA | −0.007 | 75 |

TABLE 1-continued

| Fluorophore | Polymer | Maximum Log Slope/° C. | Temp |
|---|---|---|---|
| Perylenedicarboximide (PDC) | SOA | −0.06 | 75 |
| PtOEP | GP-197 | −0.0033 | 10 |
| Pyrene | Cellulose Acetate | | |
| Pyronin B | PMMA | −0.046 | 60 |
| Pyronin Y | model airplane dope | −0.055 | 50 |
| Pyronin Y | PMMA | −0.072 | 75 |
| Pyronin Y | Polycarbonate | −0.0168 | 50 |
| Quinizarin | Polystyrene | −0.084 | 90 |
| Rhodamine B | Cellulose Acetate | −0.0167 | −125 |
| Rhodamine B | PVC | −0.014 | −5 |
| Rhodamine B | PVP | +0.057 | −30 |
| Rhodamine B | Polyurethane | −0.0175 | 80 |
| Rhodamine B | model airplane dope | −0.018 | |
| Rose Bengal | Ethyl Cellulose | −0.09 | 80 |
| Rubrene | PMMA | −0.034 | 5 |
| Rubrene | SOA | | |
| Ruthenium Comp. DJ-171 | GP-197 | | |
| Ruthenium Comp. DJ-201 | GP-197 | −0.042 | 0 |
| Ruthenium Comp. DJ-275 | GP-197 | −0.018 | 0 |
| Ruthenium Comp. VG-220-1-2 | GP-197 | −0.0573 | 10 |
| Ruthenium Comp. VG-225-2 | GP-197 | −0.0212 | −10 |
| Ruthenium Comp. VH-127 | GP-197 | −0.0071 | −150 |
| Ruthenium Comp. SC-324 | GP-197 | −0.0233 | 0 |
| Ruthenium Comp. SC-393 | GP-197 | −0.0343 | 0 |
| Ruthenium (bpy)/Zeolite | PVA | −0.0269 | 40 |
| Ruthenium (trpy) | Ethyl Cellulose | −0.0131 | −140 |
| Ruthenium (trpy) | GP-197 | −0.0134 | −140 |
| Ruthenium (trpy) | model airplane dope | | |
| Ruthenium (trpy) | PMMA | | |
| Ruthenium (trpy)/Zeolite | PVA | −0.0096 | −100 |
| Sulphorhodamine B | model airplane dope | −0.0375 | 105 |
| TTMHD | solid | −0.0293 | 25 |

Fluorescent beads were prepared containing the temperature-sensitive fluorophore, $Eu(TTA)_3$, and the temperature-insensitive fluorophore coumarin. $Eu(TTA)_3$ is optimally excited at 350 nm and emits at 614 nm (with an additional peak at 595 nm). Coumarin is optimally excited at 420–460 nm and emits at 480 nm (with an additional peak at 510 nm). At the optimal excitation for $Eu(TTA)_3$, there is no excitation of coumarin, and at the optimal excitation of coumarin, there is no excitation of $Eu(TTA)_3$. The fluorescent beads were made with either polystyrene or PMMA, that were co-embedded with $Eu(TTA)_3$ and coumarin. The fluorescence emission due to $Eu(TTA)_3$ changed 2.5% for every one degree centigrade change. Since the noise is extremely low (having a signal to noise ratio of approximately 100:1) the resolution of a change of 0.01° C. could be accurately determined.

As can be seen in FIG. 3, excitation at 350 nm resulted in a single peak of emission at 614 nm, indicative of the fluorescence of europium in the $Eu(TTA)_3$. When excited at 420 nm, there was a peak at 480 nm with minimal emission at 614 nm. The ratio of $Eu(TTA)_3$:coumarin in the beads can be adjusted so that the peak of the $Eu(TTA)_3$ emission at 614 nm observed when the excitation was performed at 350 nm, has approximately the same amplitude as the emission peak due to coumarin at 480 nm, when the excitation was performed at 420 nm (see FIG. 3).

Figure 4:
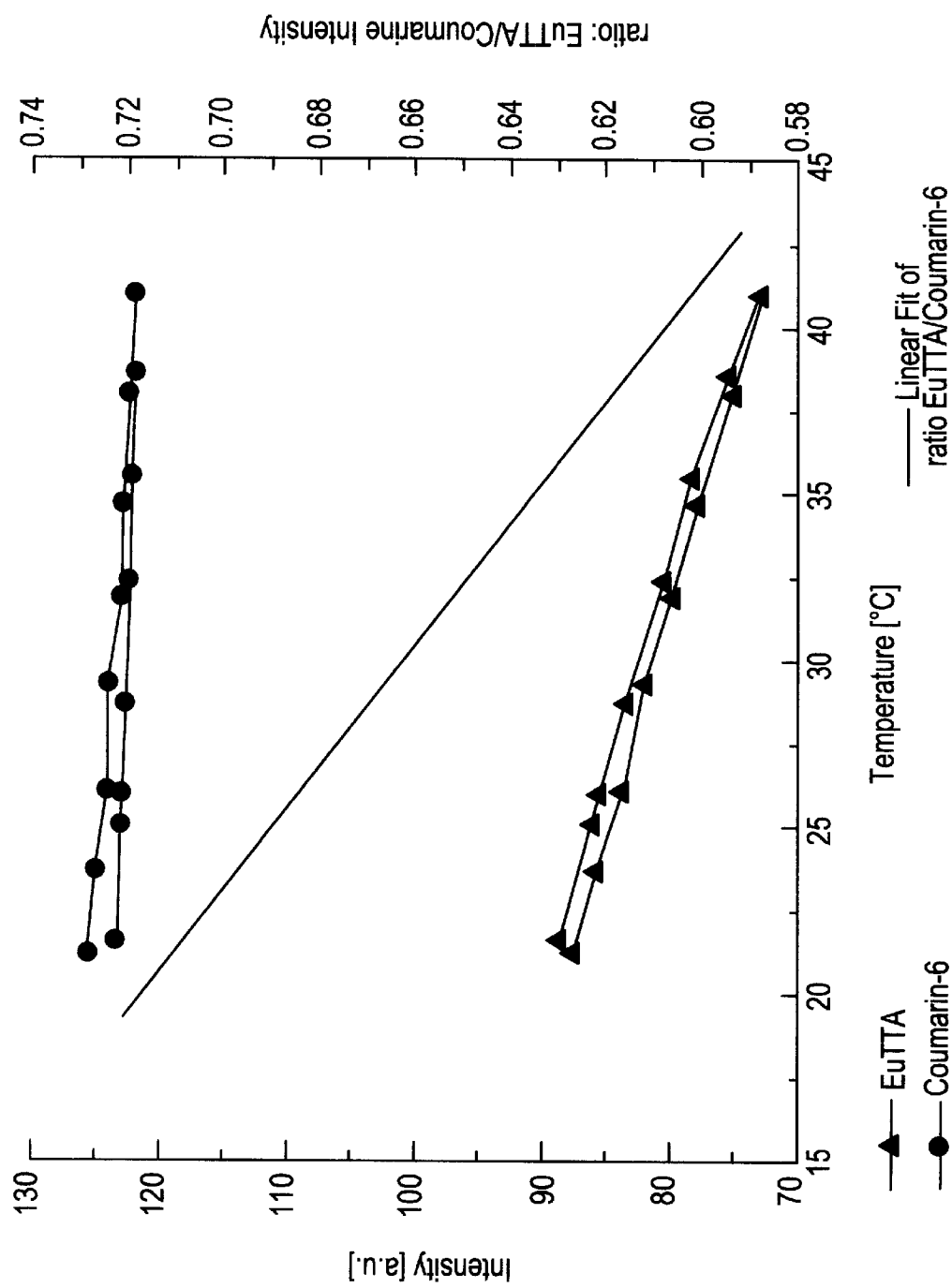
FIG. 4(upper plot) shows the change in the amplitude of the fluorescence emission at 614 nm. with temperature when the fluorescent beads were excited at 350 nm. The beads contained $Eu(TTA)_3$ and coumarin. The fluorescence change observed is due to the temperature-sensitive fluorescence of the $Eu(TTA)_3$.

The temperature sensitivity of the fluorescent beads was determined by incubating them in a cuvet and measuring the fluorescence emission from the temperature-sensitive and temperature-insensitive fluorophores. As shown at right in FIG. 4, the fluorescence emission of the $Eu(TTA)_3$ was temperature-sensitive, whereas that of coumarin was not. Therefore the properties of the beads exemplified make them appropriate for use as disclosed herein.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in there entireties.

What is claimed is:

1. A polymeric fluorescent bead comprising a temperature-sensitive fluorophore and a temperature-insensitive fluorophore embedded in a polymeric material, wherein the fluorescence emission due to the temperature-sensitive fluorophore and due to the temperature-insensitive fluorophore can be resolved.

2. The polymeric fluorescent bead of claim 1 wherein the temperature-sensitive fluorophore is $Eu(TTA)_3$.

3. The polymeric fluorescent bead of claim 1 wherein the temperature-insensitive fluorophore is coumarin.

4. The polymeric fluorescent bead of claim 1 wherein the polymer is a non-aromatic synthetic polymer.

5. The polymeric fluorescent bead of claim 4 wherein the non-aromatic synthetic polymer is poly(methyl methacrylate).

6. The polymeric fluorescent bead of claim 1 wherein the polymeric material is polystyrene.

7. The polymeric fluorescent bead of claim 1 wherein the fluorescent bead is 80–90 nm in size.

8. A polymeric fluorescent bead comprising a first and a second temperature-sensitive fluorophore both of which are embedded in a polymeric material, wherein the fluorescence emission due to the first temperature-sensitive fluorophore increases with temperature, whereas the fluorescence emission due to the second temperature-sensitive fluorophore decreases with temperature.

9. A method of determining the temperature of a cell comprising:
   (a) placing the polymeric fluorescent bead of claim 1 into a cell;
   wherein when the temperature-sensitive fluorophore and the temperature-insensitive fluorophore are excited with the appropriate light they emit detectable fluorescent signals which can be resolved from each other; and
   wherein the fluorescent signal due to the temperature-sensitive fluorophore is affected by the temperature of the cell;
   (b) exciting the temperature-sensitive and temperature-insensitive fluorophores with the appropriate light; and
   (c) measuring the intensity of the fluorescent signal emitted by the temperature-sensitive and temperature-insensitive fluorophores;
   wherein the intensity of the fluorescent signal measured for the temperature-sensitive fluorophore is indicative of the temperature of the cell when corrected for its local concentration by the corresponding intensity of the temperature-insensitive fluorophore;
   wherein the temperature is determined.

10. A method of detecting the metabolic activity of a cell comprising determining the temperature of the cell by the method of claim 9 and correlating the temperature with the metabolic activity of the cell.

11. A method of detecting the presence of abnormal metabolism of a cell surrounded by healthy tissue in a tissue sample comprising determining the temperature of the cell by the method of claim 9, wherein a difference in temperature of the cell relative to a control cell, is indicative that the cell is undergoing abnormal metabolism.

12. The method of claim 11 wherein the tissue sample is obtained from a tumor biopsy.

13. The method of claim 11 wherein the abnormal metabolism of the cell is indicative of ultraviolet damage, cachexia, or apoptosis.

* * * * *